United States Patent [19]

Chen et al.

[11] Patent Number: 5,149,867
[45] Date of Patent: Sep. 22, 1992

[54] CRYSTALLIZATION OF WATER-INSOLUBLE DICARBOXYLIC ACID

[75] Inventors: Clay T. Chen; Mary S. Chen, both of Metuchen, N.J.

[73] Assignee: Hatco Corporation, Fords, N.J.

[21] Appl. No.: 78,550

[22] Filed: Jul. 28, 1987

[51] Int. Cl.$^5$ ............................................. C07C 51/42
[52] U.S. Cl. ..................................................... 562/486
[58] Field of Search .......................................... 562/486

[56] References Cited

FOREIGN PATENT DOCUMENTS 989438  4/1965  United Kingdom .

OTHER PUBLICATIONS

Chem. Abs. vol. 77:1972:20052 (p. 2).
Chem. Abs. vol. 77:1972:5109 (pp. 451-452).
Condensed Aromatics vol. 79:1973:136897 (p. 359).
Chem. Abs. vol. 80:1974:146601 (p. 4).
Chem. Abs. vol. 80:1974:59787 (p. 344).
Chem. Abs. vol. 81:1974:120233 (p. 498).
Chem. Abs. vol. 82:1975:125175 (p. 540).
Chem. Abs. vol. 82:1975:155963 (p. 574).
Condensed Aromatics: vol. 83:1975 (pp. 369-370).
Condensed Aromatics: vol. 83:1975 (p. 487).
Condensed Aromatics: vol. 84:1976 (p. 527).
Noncondensed Aromatics: vol. 87:1977 (p. 677).
Chem. Abs. vol. 102:1985:185547 (p. 2).

*Primary Examiner*—Jose G. Dees
*Assistant Examiner*—Joseph Conrad, III
*Attorney, Agent, or Firm*—Kane, Dalsimer, Sullivan, Kurucz, Levy, Eisele and Richard

[57] ABSTRACT

The invention makes available an improved process for the crystallization and purification of a water-insoluble aromatic dicarboxylic acid, such as 2,6-naphthalenedicarboxylic acid. The process involves steps of contacting the insoluble acid with aqueous base to make a water-soluble di salt of the acid, removal of insoluble impurities to obtain a clear solution of the di salt, partial acidification of the solution by adding a water-soluble acid, holding the thus-obtained slurry of the insoluble acid and its salt for a time sufficient to allow dissolution of the initially-formed small particles of the insoluble acid and the formation of large well-formed crystals, then acidifying the slurry further to convert remaining salts to the insoluble acid, and recovering this acid. The crystallization can be accelerated by recycling product and by adding surfactants, and can be operated in a continuous mode. 2,6-Naphthalenedicarboxylic acid thus crystallized is readily dried, non-sticky, non-dusty, and of high purity.

10 Claims, No Drawings

CRYSTALLIZATION OF WATER-INSOLUBLE DICARBOXYLIC ACID

BACKGROUND OF THE INVENTION

1. Field of the Invention

The invention relates to a method for the crystallization of a substantially water-insoluble aromatic dicarboxylic acid to obtain large easily-handled crystals of high purity. The method is particularly applicable to the extremely water-insoluble aromatic dicarboxylic acid, 2,6-naphthalenedicarboxylic acid, which is difficult otherwise to purify and crystallize.

2. Brief Description of the Prior Art

Aromatic dicarboxylic acids are major industrial intermediates for the preparation of condensation polymers, especially thermoplastic polyesters and polyamides. These are used in films, fibers, machine parts, electrical parts, containers, and the like. For these applications, it is important that the aromatic dicarboxylic acid be made available to the polymer manufacturer in high purity, free of water or other solvents, and in easily-handled, non-dusty, non-sticky form. Purification by crystallization would seem to be a reasonable way to accomplish these requirements, but crystallization of the very water-insoluble aromatic dicarboxylic acids has been difficult and challenging. A particularly difficult case because of its extreme water insolubility is 2,6-naphthalenedicarboxylic acid.

2,6-Naphthalenedicarboxylic acid (hereinafter called 2,6-NDA) is a product which can be made by oxidation of 2,6-di-lower-alkylnaphthalene, or by disproportionation of naphthalenecarboxylic acid salts, said precursors having been made by oxidation of monoalkylnaphthalenes. Commercially feasible routes are known which employ molecular oxygen as the oxidant.

2,6-NDA is a useful intermediate for making condensation polymers of the polyester and polyamide types, having advantageous properties. For example, linear polyesters and polyamides made from 2,6-NDA, in comparison to analogous polymers made from terephthalic acid, can have superior thermal, mechanical, optical, and electrical properties.

These advantages of 2,6-NDA in linear condensation polymers are best achieved by use of 2,6-NDA in a high state of purity. Impurities such as the monoaldehyde monocarboxylic acid analog of 2,6-NDA act as chain ends and limit the achievable molecular weight, whereas impurities such as benzenetricarboxylic acids cause chain branching and limit the linearity, with generally adverse effects on polymer mechanical properties. Aldehyde and metal impurities also have adverse effects on color, clarity, electrical properties, and processability. Therefore, it is important to have effective and economical processes for purification of 2,6-NDA to remove or substantially reduce these and other impurities which otherwise will be found in industrially produced 2,6-NDA.

Because of the difficulty of crystallizing 2,6-NDA, many process designers have avoided doing so and instead have chosen to conduct the purification step on an ester or a salt of 2,6-NDA and then subsequently convert said ester or salt back to 2,6NDA; for example, Norton (to Sun Ventures Inc.), U.S. Pat. No. 3,965,160 (Jun. 22, 1976). In this patent, air oxidation is used while the 2,6-NDA is in the form of a salt, to remove metals. Teijin Ltd., in Japanese Kokai 50/160248 (Dec. 25, 1975) [Chem. Abs. 84:150408] describe purifying the monopotassium salt of 2,6-NDA and then converting back to 2,6-NDA by adding hydrochloric acid.

Other proposed processes involve use of organic solvents to extract impurities from 2,6-NDA. Norton, Ger. Appl. 2331251 (January 1974) [Chem. Abs. 80: 146601] teaches use of acetic acid and toluene or xylene, and Norton in Ger. Appl. 2400964 (July 1974) [Chem. Abs. 81: 120233] teaches the use of xylene, ethylbenzene or tetralin. Kulakov et al., Russian Patent 486008 (September 1975) [Chem. Abs. 83: 206016] teaches the use of aliphatic acids as solvents for purifying 2,6-NDA. Crystallization of 2,6-NDA from its own melt is impracticable because the compound melts above 300 degrees C with decomposition.

The processes which involve the use of a solvent entail solvent losses and/or the cost of solvent recovery, and the risk of air pollution by solvent vapors. It is also difficult to assure complete removal of solvent from the product.

Processes which require esterification, purification of the ester, and hydrolysis back to acid inherently require two extra chemical steps with inherent costs and usage of reagents.

Processes, such as the Teijin process mentioned above, which involve purification of the salt in aqueous solution followed by reacidification and recovery of 2,6-NDA can be effective in removing certain of the impurities but they have a non-obvious problem which imposes a serious difficulty. When 2,6-NDA is precipitated from its salts by addition of an acid such as hydrochloric, sulfuric or acetic, the 2,6-NDA forms a very fine suspension, in which the small particles appear to be of amorphous or microcrystalline nature. When this suspension is centrifuged or filtered out, the filter cake will contain large amounts of the aqueous solution (the "mother liquor") up to 70 percent. A filter cake of this sort, containing a large amount of the mother liquor, is hard to suck dry and hard to wash free of impurities. When such filter cakes are dried, the product 2,6-NDA is a very light dusty and electrostatically charged powder which is very difficult to handle, and not very pure. In this dusty form, it can present a fire and inhalation hazard. None of the prior art purification schemes address this problem of obtaining easily handled non-dusty non-sticky large crystals.

Simple recrystallization of 2,6-NDA from water fails because of the low solubility of 2,6-NDA even in very hot water, less than 0.1% at 100 deg. C. Digestion of the small amorphous or microcrystalline particles of 2,6-NDA in hot water fails to bring about redeposition to the desired large well-formed rapid-settling crystals. The crystal growth process known as "ripening" or "Ostwald ripening", where a slurry of small crystals is converted to a rapid settling dispersion of large crystals by aging the slurry is found to fail when applied to 2,6-NDA.

It is an object of the present invention to make available a convenient and effective process for making purified 2,6-NDA from relatively impure 2,6-NDA without the use of organic solvents, without the need for esterification and hydrolysis, and with the formation of rapid-settling, easily-filtered, easily-dried, non-sticky, non-dusty large crystals of 2,6-NDA. It is a further object of the invention to make available a purification process for 2,6-NDA which permits removal of undesirable impurities and formation of easily-handled crystals.

It is a further object of the invention to make available a method for preparing purified well-formed crystals of other substantially water-insoluble aromatic dicarboxylic acids. By substantially water-insoluble is meant a solubility of less than 0.1% in water at 100 degrees C. Examples of such acids include the other isomers of naphthalenedicarboxylic acid, as well as 4,4'-oxydibenzoic acid, and 1,1,3-trimethyl-3-phenylindan-4',5-dicarboxylic acid.

SUMMARY OF THE INVENTION

Most broadly, the invention comprises contacting a water-insoluble aromatic dicarboxylic acid in an aqueous slurry containing crystals of the mono salt, until the original small particles of said acid have been replaced by large well-formed crystals.

As specifically applied to 2,6-NDA, the invention comprises contacting 2,6-NDA in the form of an aqueous slurry in which the aqueous dissolved phase contains a salt of 2,6-NDA, said salt being partially present as crystalline mono salt and partially as dissolved salt, until substantial dissolution of the crude particles of 2,6-NDA has occurred and the 2,6-NDA has reappeared from solution as large crystals in a high state of purity.

DETAILED DESCRIPTION OF A PROCESS OF THE INVENTION

The process of the invention is carried out starting with 2,6-NDA in a technical or crude grade of purity, substantially less pure than the desired polymerization grade. If the technical 2,6-NDA is made from catalyzed oxidation of 2,6di-lower-alkylnaphthalene, it can be expected to contain incomplete oxidation products such as 6-formyl-2-naphthalenecarboxylic acid and over-oxidation products such trimellitic acid. Moreover, it may contain other NDA isomers if the starting dialkylnaphthalene was not isomerically pure, and it may also contain various heavy metals from the oxidation catalyst and from the materials of construction of the process equipment. If made by ammonoxidation and hydrolysis of dinitrile, it may contain imide, amide, and nitrile impurities. Metals which occur in technical 2,6-NDA are typically cobalt, iron, and sometimes nickel, chromium, and manganese.

A preferred embodiment of the process of the invention is conducted starting with the crude 2,6-NDA as produced commercially by oxidation of a di-lower-alkylnaphthalene. The acid is put into aqueous solution by addition of about two moles, or preferably slightly less than two moles, of alkali per mole of acid. The alkali can be, for example sodium hydroxide, sodium carbonate, sodium bicarbonate, potassium hydroxide, potassium carbonate, or potassium bicarbonate, or mixtures thereof. Ammonia (ammonium hydroxide) can be used. It will be recognized by one skilled in the art that other bases which form water-soluble di salts and less water soluble mono salts could be used as equivalents of the aforementioned bases, for example, lithium bases, and substituted ammonia bases (amines) but these are more costly and have no advantage. Some impurities will generally be found not to dissolve at this stage; they are believed to include some of the heavy metal impurities resulting from the oxidation catalyst and from corrosion. These insoluble impurities are removed by filtration, centrifugation, or settling and decantation at this stage; for removal of color bodies, it has been found advantageous to filter with activated charcoal at this stage. A particularly advantageous embodiment of the purification process is to employ an alkali metal carbonate (added or made in situ by passing in carbon dioxide into the alkaline solution) as all or part of the base used to make the soluble di salt of 2,6-NDA; any insoluble metal carbonates are easier to filter than the usually colloidal or gelatinous metal hydroxides which form when the alkali metal hydroxides are used as the base.

Once the clear di salt solution of 2,6-NDA has been prepared, which can be up to concentrations of di salt in the vicinity of 20% in the case of the disodium salt, the next step in a preferred embodiment of the invention is partial acidification to form a slurry of small amorphous or microcrystalline particles of 2,6-NDA plus the mono salt, which most generally will be partly present as crystals (readily recognized in the case of the mono sodium salt as platelike crystals), partly in solution, and any remaining di salt which will be in solution. As mentioned, the di salt is very soluble, up to about 20% in the case of the disodium salt, but the mono salt is rather low in solubility, in the vicinity of 1% in the case of the mono sodium salt and even less in the case of the ammonium salt. This partial acidification step requires an amount of an acid sufficient to liberate from 1 to 98%, preferably 30 to 90%, of the free 2,6-NDA from its salt. At this point, the process mixture contains the free 2,6-NDA, the mono salt which is more water soluble but at the preferred process concentrations is generally partly out of solution as crystals, and any di salt still present, which will be in solution. Because of the close acidity values of the two carboxyl groups of 2,6-NDA, the free 2,6-NDA solid, the partially water soluble mono salt, and the very soluble di salt can all coexist in equilibrium.

Then, in a critical and characteristic step of our inventive process, the slurry is held in the partially acidified state for a length of time, as discussed hereinbelow. In this state, the initially-produced amorphous or microcrystalline small particles of impure 2,6-NDA disappear and are replaced by large well-formed prismatic crystals of highly pure 2,6-NDA. By large is meant that the smaller dimension of the crystal prisms is not significantly smaller than about 10 microns, and by well-formed is meant that the crystals have visible faces and angles, and are substantially transparent, in contrast to the initial amorphous or microcrystalline particles which are generally of 1 micron or smaller size, lack well defined faces, and are poor transmitters of light. Lacking x-ray diffraction data, it is not known whether these amorphous or microcrystalline particles have internally a crystal lattice structure.

That the above-described crystallization phenomenon occurs is surprising in view of the extreme water insolubility of 2,6-NDA, and may be attributable to some sort of equilibrium involving the acid and its mono and di salts. It is surprising and unexpected that the presence of the crystals of the mono salt appear to be important for the desired crystallization to take place at a useful rate. This is not the same as the phenomenon of seeding, which is conducted by adding the same species of crystals as those to be produced and generally to a supersaturated solution of the same compound.

The thus-obtained fast settling crystal slurry can then be filtered or centrifuged, to obtain a low water content cake of 2,6-NDA contaminated principally with the mono salt. To avoid having the mono salt in the filter cake of 2,6-NDA, a further step of acidification is conducted to convert this salt to 2,6-NDA. Conditions for this second step of acidification are discussed in more detail hereinbelow. Once the large crystals have been formed during the holding period following the initial acidification, this second stage of acidification gives additional large crystals rather than the amorphous or microcrystalline small particles which might have been expected based on experience with direct one-step acidification.

In our inventive process, the crystal reformation of the solid 2,6-NDA in the presence of its salt is critical; if an attempt is made to filter out the 2,6-NDA immediately after it has been precipitated from its salt, a poorly-filterable and poorly-drainable wet mass of microcrystalline or amorphous relatively impure 2,6-NDA is obtained, retaining up to about 70% water in a sticky cake. Moreover, the prior art method of acidifying the di salt to the diacid in one step gives the poorly formed amorphous or microcrystalline 2,6-NDA with the disadvantageous properties already referred to.

The partial acidification step and holding step of the invention are conducted at from about 0 to about 200 deg. C, but preferably not above the atmospheric boiling point of the solution which will normally be slightly above 100 deg. C. At above this normal boiling point, the process will require an autoclave to prevent loss of water.

The choice of acid for the acidification is not critical, all that is required is that it be water soluble and capable of converting the carboxylate salt groups of 2.6-NDA to carboxylic acid groups. Thus, mineral acids such as hydrochloric, sulfuric, nitric and phosphoric acids, or organic acids such as acetic, glycolic, or lactic can be used, the choice being based on cost and handling convenience, and thus tending to favor use of hydrochloric, sulfuric, or acetic acids.

The requisite waiting time following the initial (partial) acidification will vary with the temperature but will typically be in the range of 1 minute to 100 hours, preferably 10 minutes to 24 hours. It has been found that the time can be shortened by recycling some of the well-crystallized 2,6-NDA from an earlier batch; with an effective amount of such recycled crystals, typically 1% or more relative to the amount of 2,6-NDA to be formed in the current cycle, the waiting time for good crystal formation can be perceptibly shortened; with about 10% of recycled crystals relative to the amount of 2.6-NDA to be formed, the time can be about one-fifth to one-half that required without recycled crystals; with 100% or more of recycled crystals relative to the amount of 2,6-NDA to be formed, the time can as short as a minute. As will be discussed further hereinbelow, the time can be shortened also with other attendant advantages by having a surface active agent present. With such foreshortened process times, the process can be made to run in a continuous or semicontinuous fashion. It is surprising that this introduction of well formed crystals of 2,6-NDA speeds up our process, since mere seeding of a slurry of small amorphous or microcrystalline 2,6-NDA does nothing. Even in this continuous mode of running the process, it is important that the partial acidification feature be retained, and it is preferable not to acidify to more than 90% of complete conversion of all carboxylate groups to carboxylic acid groups.

The point of completion of the change from amorphous or microcrystalline small particles to large well-formed crystals can be observed visually, preferably with the aid of a magnifying glass or microscope (the thick prisms of the 2,6-NDA are readily distinguishable from the opaque small particles as well as from the flat plate of mono salt), or by noting the point at which the settling time of the slurry becomes short (such as 0.1 to 10 minutes depending on vessel size) indicating that only large crystals are present. The settling time can be observed on a sample or by stopping the agitation and observing the settling of the entire reactor contents through a sight glass. It will be evident to one skilled in the art of chemical manufacture that once the optimum time is set for a particular operating temperature, further batches may be run without the necessity of direct visual observations, by careful adherence to the same times and temperatures for each batch. The required time for the completion of the transformation from small amorphous or microcrystalline particles to large well-formed crystals will be dependent on temperature as are most rate processes; the required time will be at the upper end of the aforementioned range if the process is conducted near the lower end of the aforementioned temperature range, and conversely, the required time will be at the lower end of the aforementioned range if the process is conducted near the upper end of the said temperature range. It is a feature of our process that this waiting time be provided for the crystallization to proceed to substantial completion, before all of the salt is acidified.

The concentrations of 2,6-NDA salts in the initial solution can be in the range of from 1% to about 20%. Below 1%, the mono salt may be entirely in solution so that it does not function to aid crystallization at any useful rate, whereas concentrations above about 20% are merely inconvenient because of difficult stirrability of the slurry, and with appropriately powerful stirring motors, it is possible to operate well above 20%, such as up to 50%. Within such a wide range, concentration does not appear to be a critical variable in our process.

The well-crystallized 2,6-NDA can then be recovered by filtration, centrifugation, or settling and decantation, and subsequently dried. Since under the conditions of the inventive process, the mono salt of 2,6-NDA is partly out of solution, it is preferable to convert this salt to acid before attempting to recover the product 2,6-NDA; otherwise, a mixed filter cake will be obtained comprising 2,6-NDA and its salt. Although it is possible to convert this salt to 2,6-NDA on the filter by washing the filter cake with an acid, or by leaching out the salt from the filter cake with copious amounts of water, it is most convenient to convert the salt to 2,6-NDA in the slurry before recovering the 2,6-NDA. This step of converting salt to acid can readily be done by performing a final stage of acidification, to pH 4.5 or below, prior to recovery of the 2,6-NDA. Some advantage is also found in not acidifying to below pH 1 in this final acidification, the advantage being that some organic acid impurities are thereby left in solution; these impurities, believed to the other aromatic carboxylic acids such as trimellitic acid, can be forced out of solution by excessive strong acid, and can then coprecipitate with the 2,6-NDA if the pH is reduced much below 1.

An advantageous feature of our inventive process is that in this final acidification, unlike a direct one-step acidification of a 2,6-NDA salt to 2,6-NDA, the 2,6-NDA comes out as good crystals. It is surprising in view of the aforementioned failure of seeding or "ripening" to reform a slurry of amorphous or microcrystalline 2,6-NDA.

A further improvement on our basic process is our discovery that by including a surfactant (surface active agent), the rate of the conversion from small amorphous or microcrystalline particles to large well-formed crystals is accelerated, and moreover, more uniform crystals are obtained. A wide variety of surface active agents can be used such as anionics exemplified by alkylarylsulfonates, alkyl sulfate salts, alkyl acid phosphate salts, and alkylpolyoxyethylene acid phosphate salts, cationics exemplified by tetraalkylammonium salts, and nonionics exemplified by alkylaryl polyoxyethylene ethers and block copolymers of ethylene oxide and propylene oxide. By surface active agents we mean to include those substances commonly designated as "phase transfer catalysts" which typically include middle chain length tetraalkylammonium salts (exemplified by tetrabutylammonium chloride), higher-alkyltrimethylammonium salts and bis(higher-alkyl)dimethylammonium salts (exemplified by the commercial Arquad products of AKZO), polyoxyethylenes (exemplified by the Polyox products of Union Carbide), mono- and dialkyl ethers of said polyoxyethylenes, and the macrocyclic polyolefin oxides (the so-called crown ethers). Concentrations of from 0.001 to 10% are suitable, preferably 0.005 to 2%. A preferred surface active agent class because of good efficacy in the embodiment of our process involving the sodium salts is the class of water-soluble alkylaryl polyoxyethylene ether surfactants (exemplified by the Tritons of Rohm & Haas Co.). A preferred class of water-soluble surfactants in connection with the ammonium salt version of our process is the class of water-soluble quaternary surfactants, such as dimethyldicocoammonium chloride or trimethylcocoammonium chloride (Arquads made by AKZO).

The following examples describe the manner and process of the invention and set forth the best mode contemplated by the inventor, but are not to be construed as limiting.

EXAMPLE 1

The crude 2,6-NDA used in this and following examples had an assay as follows (by GC): 95% 2,6-NDA, 1% trimellitic acid, 0.2% 6-formyl-2-naphthoic acid, plus various metallic impurities and unidentified color bodies.

To a stirred reaction vessel containing 1200 gallons of water, 1000 lbs. of crude 2,6-NDA was added and then 717 lbs. of 50% sodium hydroxide which put most of the solids into solution and resulted in a pH of 12. Then, 10 lbs. of carbon dioxide was introduced (as dry ice) which lowered the pH to 7.3 and produced a readily filterable composition of soluble di salt and some insoluble impurities. After addition of 50 lbs. of Nuchar activated charcoal to remove color bodies, the reactor contents were filtered to obtain a clear solution of the disodium salt.

The filtrate was partially acidified to pH 6.5 by addition of 15% hydrochloric acid (in an amount corresponding to one-half of the sodium carboxylate groups originally present in the disodium salt solution) with good stirring at 110–120 deg. F. At this point, microscopic examination showed 2.6-NDA in the form of small opaque amorphous or microcrystalline particles. The stirred mixture was then heated to 160 deg. F over 6 hours until the first appearance of large prisms of well-crystallized 2,6-NDA, along with thin platelets of the monosodium salt (as seen by microscopic examination of a sample). Then the temperature was raised to 200 deg. F over about one hour to speed up the crystallization, and held at 200 deg. F for about two hours. At this point, microscopic examination of a sample showed substantial absence of the small amorphous or microcrystalline particles and essentially of the 2.6-NDA had been converted to large prisms. When stirring was stopped, the suspension settled in about 5 minutes. Then with stirring at 200 deg. F, the reactor contents were acidified down to pH 4 to 4.5 by further addition of 15% hydrochloric acid, and shortly after completion of addition of the last hydrochloric acid, the slurry was filtered hot. The product filtered and drained well, and was finally dried in an oven to a non-dusty, non-sticky solid.

A yield of 916 lbs. (96% of the 2,6-NDA in the original crude) was recovered, in a purity of 99.9% as determined by GC. The color of the product as measured by absorption was 0.07. and the inorganic content was less than 20 parts per million.

In the following examples, the 2,6-NDA salt solution was made from commercial 2,6-NDA with an assay as given above. This crude 2,6-NDA is dissolved in an equivalent amount of dilute sodium hydroxide plus sodium carbonate solution, treated with charcoal to remove color, and filtered. The solution thus obtained has a concentration of from 9% to 14%. The ammonium salt solution is made in the same way but using excess of dilute ammonium hydroxide.

EXAMPLE 2

In a flask fitted with agitator, thermometer, addition funnel, and vent tube is placed 1000 ml. of the 2,6-NDA disodium salt solution containing salt equivalent to 96 g. 2,6-NDA, plus 0.25 g. of Triton X-100 (a non-ionic alkylaryl polyoxyethylene ether wetting agent made by Rohm & Haas Co.). The solution is stirred and heated to 50 degrees C. and acidified with 10 ml. of 25% acetic acid. Stirring is continued until the separated monosodium salt becomes completely crystalline and settles easily (as observed by briefly stopping the stirrer). Acidification with 25% acetic acid is resumed while raising the temperature to 75–80 degrees C., until 50% of the equivalent amount (for two carboxyl groups) of the acid is added. The pH at this stage is in the range of 6 to 7. The slurry appears very thick and pasty. When viewed under a microscope, the slurry is seen to consist of large transparent monosodium salt platelets and very small opaque 2.6-NDA (acid) particles of about 1 micrometer size. Stirring is continued at this temperature for about 24 hours, while the temperature is slowly raised to 90 deg. C. Samples are taken intermittently for examination under the microscope. Transparent rhombic crystals of about 2–3 micrometer size appear slowly and increase in size and quantity. When the crystallization is complete, the very small opaque particles will have disappeared, being replaced by large (above 20 micrometers) transparent well-formed rhombic crystals. At the same time, the monosodium salt crystals will have decreased in quantity. At this time, the temperature is raised to 90–95 degrees C. and 15% hydrochloric acid is added to a pH of 4–4.5. After agitation for 30 minutes, the mixture is filtered. The filter cake is found to be loosely packed, containing only 3–10% water and it is easily dried to a free-flowing, non-dusty, non-electrostatic, non-sticky powder with a purity by GC of 99.9%. The average size of the crystals is 20×40 micrometers to 60×100 micrometers.

EXAMPLE 3

The procedure of the preceding example is repeated except the acidification is carried out with acetic acid to 75% of the equivalent amount. The results are similar to those in example 2.

EXAMPLE 4

The procedure of example 2 is repeated but instead of acetic acid, 15% hydrochloric acid is added, very slowly with good mixing to avoid local overacidification. After completing the process otherwise as described in example 2, similar results to example 2 are obtained.

EXAMPLE 5

The process is conducted exactly like example 2 but no Triton X-100 is added. The crystalline product obtained is like that in example 2 but of more irregular size.

EXAMPLE 6

The process is conducted as in example 2 but an 8% solution of the diammonium salt of 2,6-NDA is used instead of the disodium salt. The results are similar to those described in example 2. A variation of this experiment was also run wherein 0.1–0.2 g/l of Arquad 16, a long-chain alkyl methylammonium quaternary surfactant, was added prior to the acidification. The formation of large crystals proceeded more rapidly and they were visibly more uniform than without the quaternary.

EXAMPLE 7

A flask is fitted with a stirrer, thermometer, vent tube, and two addition funnels, one funnel containing 15% hydrochloric acid and the other funnel containing 12.5% aqueous solution of the disodium salt of 2,6-NDA. Into the flask is placed 100 g. of well-formed 2,6-NDA crystals as a slurry from a previous crystallization done in accordance with a batch process such as described in example 2. Then, 400 ml. of the disodium salt solution is added and the mixture agitated while the temperature is raised to 80-85 degrees C. Examination of the slurry under the microscope after 15 minutes agitation reveals a nicely crystallized monosodium salt of 2,6-NDA plus 2,6-NDA crystals. Hydrochloric acid (15%) is then added up to 70-90% of the amount equivalent to sodium carboxylate groups. This transforms the monosodium salt into more large crystals of 2,6-NDA. A second 400-600 ml. amount of the disodium salt solution is then added and acidified with 15% hydrochloric acid again to 70-90% of the equivalent amount. This process is repeated until the flask is almost full. The pH is adjusted to 4-4.5 and the contents are filtered to obtain crystalline 2,6-NDA as large easily-dried crystals of over 99% quality.

EXAMPLE 8

The procedure of example 7 was repeated except that instead of starting with crystallized 2,6-NDA, instead, 100 g. of amorphous or microcrystalline 2,6-NDA was added, and the slurry was agitated 2 hours. The initial 2,6-NDA particles are completely transformed to large well-formed crystals of 2,6-NDA. The sequential addition can be continued as in example 8.

EXAMPLE 9

The process of example 7 was repeated, except that after the first charge of 2,6-NDA disodium salt solution, the disodium salt solution and the hydrochloric acid are added simultaneously and continuously in a proportion such that at any time the hydrochloric acid amounts to 30-90% of the amount equivalent to the sodium salt. Well-formed large crystals of 2,6-NDA are obtained. The addition rate of the disodium salt solution is about 300 ml./hour, which can be increased or decreased without significant change in the quality of the crystals produced. The retention time of the slurry in the reactor is adjusted to be long enough to allow the large well-formed crystals to form; typically, retention times of 5 minutes or more are suitable. The product can be recovered by continuous or intermittent filtration of the reactor contents.

When 95% of the theoretical hydrochloric acid is used, instead of a maximum of 90% as in the foregoing, the 2,6-NDA produced is a mixture of well-formed large crystals and small amorphous or microcrystalline particles, and when 98-100% of the theoretical acid is used, the slurry is practically devoid of large well-formed crystals and is difficult to filter.

EXAMPLE 10

In like manner to example 2, one mole of crude 4,4'-oxydibenzoic acid is reacted with two moles of sodium hydroxide, filtered, the filtrate acidified with one mole of hydrochloric acid, then stirred until by microscopic examination, large well-formed crystals of the pure 4,4'-oxydibenzoic acid are predominant. The product is isolated as in example 2.

These examples are intended to be illustrative and not limiting.

What is claimed is:

1. A process for the crystallization of an aromatic dicarboxylic acid, having water solubility of less than 0.1% at 100 degrees Centigrade and being initially in the form of small particles, which comprises; reacting, in an aqueous medium, said acid and a base selected from an alkali and ammonia to prepare an aqueous slurry comprising said small particles of said acid, crystals of a mono salt of said acid and said base, a solution of a di salt of said acid and said base, and from 0 to 10% of a surfactant, maintaining said acid in said slurry until said small particles of said acid have dissolved and have been replaced by large well-formed crystals of said acid.

2. A process according to claim 1 wherein said aromatic dicarboxylic acid is selected from the group consisting of a naphthalenedicarboxylic acid, 4,4'-oxydibenzoic acid and 1,1,3-trimethyl-3-phenylindan-4'5-dicarboxylic acid.

3. A process according to claim 1 wherein said acid is 2,6-naphthalenedicarboxylic acid.

4. A process for the crystallization of 2,6-naphthalenedicarboxylic acid, initially in the form of small particles, which comprises; preparing an aqueous slurry by reaction of said acid and a sodium alkali, said slurry comprising small particles of said acid, crystals of mono sodium salt of said acid and said alkali and a solution of disodium salt of said acid and said alkali, said slurry also containing from 0 to 10% of a surfactant and maintaining said slurry until said small particles of said acid have dissolved and have been replaced by large well-formed crystals of said acid.

5. A process for the crystallization of 2,6-naphthalenedicarboxylic acid, initially in the form of small particles, which comprises; preparing an aqueous slurry comprising said small particles of said acid, crystals of a mono ammonium salt of said acid and a solution of a diammonium salt of said acid, and from 0 to 10% of a surfactant; and maintaining said slurry until said small particles of said acid have dissolved and have been replaced by large well-formed crystals of said acid.

6. A process for the preparation of 2,6-naphthalenedicarboxylic acid, which comprises; contacting said 2,6-naphthalenedicarboxylic acid, initially in the form of small particles, with an aqueous base selected from an alkali and ammonia, to make an aqueous solution of di salt of said 2,6-naphthalenedicarboxylic acid and said base, removing insoluble impurities from said solution by a method selected from filtration, centrifugation, and settling followed by decantation, to obtain a clear solution of di salt of said 2,6-naphthalenedicarboxylic acid and said base, partial acidification of said clear solution by addition of sufficient of a water-soluble acid to partially liberate said 2,6-naphthalenedicarboxylic acid from said salt, to obtain a slurry comprising small particles of said 2,6-naphthalenedicarboxylic acid, crystals of mono salt of said 2,6-naphthalenedicarboxylic acid and said base and a solution of di salt of said 2,6-naphthalenedicarboxylic acid and said base, holding the thus-obtained slurry for a time sufficient to allow dissolution of the initially-formed small particles of said 2,6-naphthalenedicarboxylic acid and appearance of large well-formed crystals of said 2,6-naphthalenedicarboxylic acid, then acidifying said held slurry to convert said salts to large well-formed crystals of said 2,6-naphthalenedicarboxylic acid, and recovering large well-formed crystals of said 2,6-naphthalenedicarboxylic acid.

7. A process according to claim 6 wherein the amount of acidifying acid added to partially liberate said 2,6-naphthalenedicarboxylic acid is from 1 to 98% of the theoretical amount required for complete liberation.

8. A process according to claim 6 wherein the amount of acidifying acid added to partially liberate said 2,6-naphthalenedicarboxylic acid is from 30% to 90% of the theoretical amount required for complete liberation.

9. A process for the purification of 2,6-naphthalenedicarboxylic acid which comprises the steps of dissolving the crude acid in water by adding substantially the equivalent amount of alkali, filtering out impurities, acidifying first to a pH of about 6 to 7 by adding a water soluble acid to the mixture, holding the acidified mixture until a fast settling slurry of large well-formed crystals is obtained, then acidifying further by adding hydrochloric acid in a limited amount only sufficient to reduce the pH to about pH 4–5 and filtering to obtain purified 2,6-naphthalenedicarboxylic acid as large crystals.

10. A process according to claim 1 wherein from 0.001 to 10% of a surfactant is present during the crystallization.

* * * * *